United States Patent [19]

Haaga

[11] Patent Number: 4,708,147
[45] Date of Patent: Nov. 24, 1987

[54] UNIVERSAL BIOPSY NEEDLE

[76] Inventor: John R. Haaga, 3409 N. Hilltop, Chagrin Falls, Ohio 44022

[21] Appl. No.: 945,226

[22] Filed: Dec. 19, 1986

Related U.S. Application Data

[63] Continuation of Ser. No. 705,051, Feb. 25, 1985, abandoned, which is a continuation-in-part of Ser. No. 625,356, Jun. 27, 1984, abandoned.

[51] Int. Cl.[4] .............................................. A61B 10/00
[52] U.S. Cl. ................................. 128/753; 128/305; 128/754
[58] Field of Search ......................... 128/751–755, 128/305–318

[56] References Cited

U.S. PATENT DOCUMENTS

| | | | |
|---|---|---|---|
| 1,663,761 | 3/1928 | Johnson | 128/751 |
| 2,219,605 | 10/1940 | Turkel | 128/754 |
| 2,827,039 | 3/1958 | Seiger | 128/750 |
| 2,919,629 | 1/1960 | Ackerman | 128/305 |
| 3,606,878 | 9/1971 | Kellogg | 128/750 |
| 3,732,858 | 5/1973 | Banko | 128/305 |
| 3,844,272 | 10/1974 | Banko | 128/305 |
| 3,995,679 | 12/1976 | Glatzer | 128/305 |
| 4,396,021 | 8/1983 | Baumgartner | 128/754 |
| 4,403,617 | 9/1983 | Tretinyak | 128/754 |
| 4,461,305 | 7/1984 | Cibley | 128/754 |
| 4,487,209 | 12/1984 | Mehl | 128/754 |
| 4,512,344 | 4/1985 | Barber | 128/305 |
| 4,530,356 | 7/1985 | Helfgott et al. | 128/305 |

FOREIGN PATENT DOCUMENTS

| | | | |
|---|---|---|---|
| 483978 | 12/1975 | U.S.S.R. | 128/753 |
| 567447 | 9/1977 | U.S.S.R. | 128/754 |

Primary Examiner—William E. Kamm
Assistant Examiner—Max F. Hindenburg
Attorney, Agent, or Firm—Body, Vickers & Daniels

[57] ABSTRACT

A cannula for a biopsy needle is provided with an axially and circumferentially open end forming cutting edges for severing tissue upon insertion or rotation at a lesion side. Concentric cannulas may be used for electively performing end cutting biopsy sampling or side cutting biopsy sampling with a single instrument.

21 Claims, 22 Drawing Figures

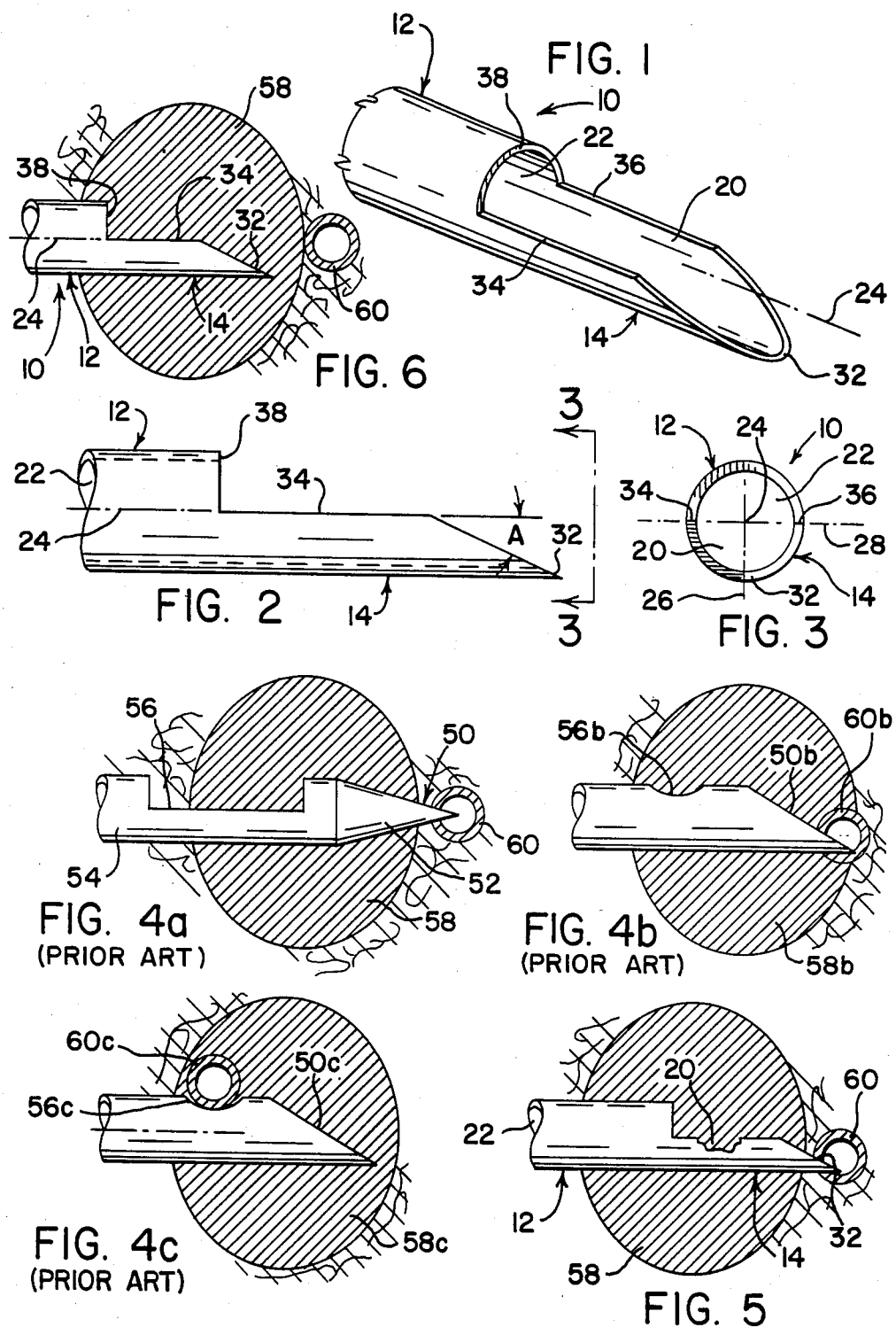

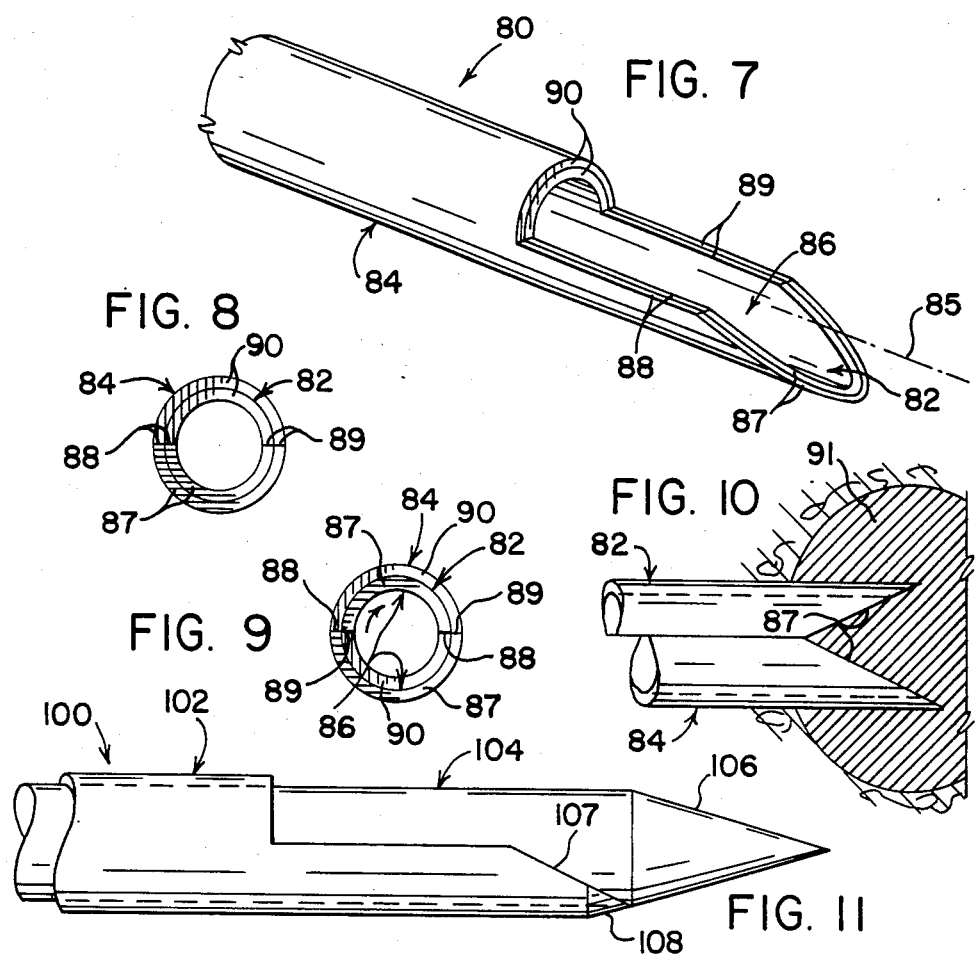

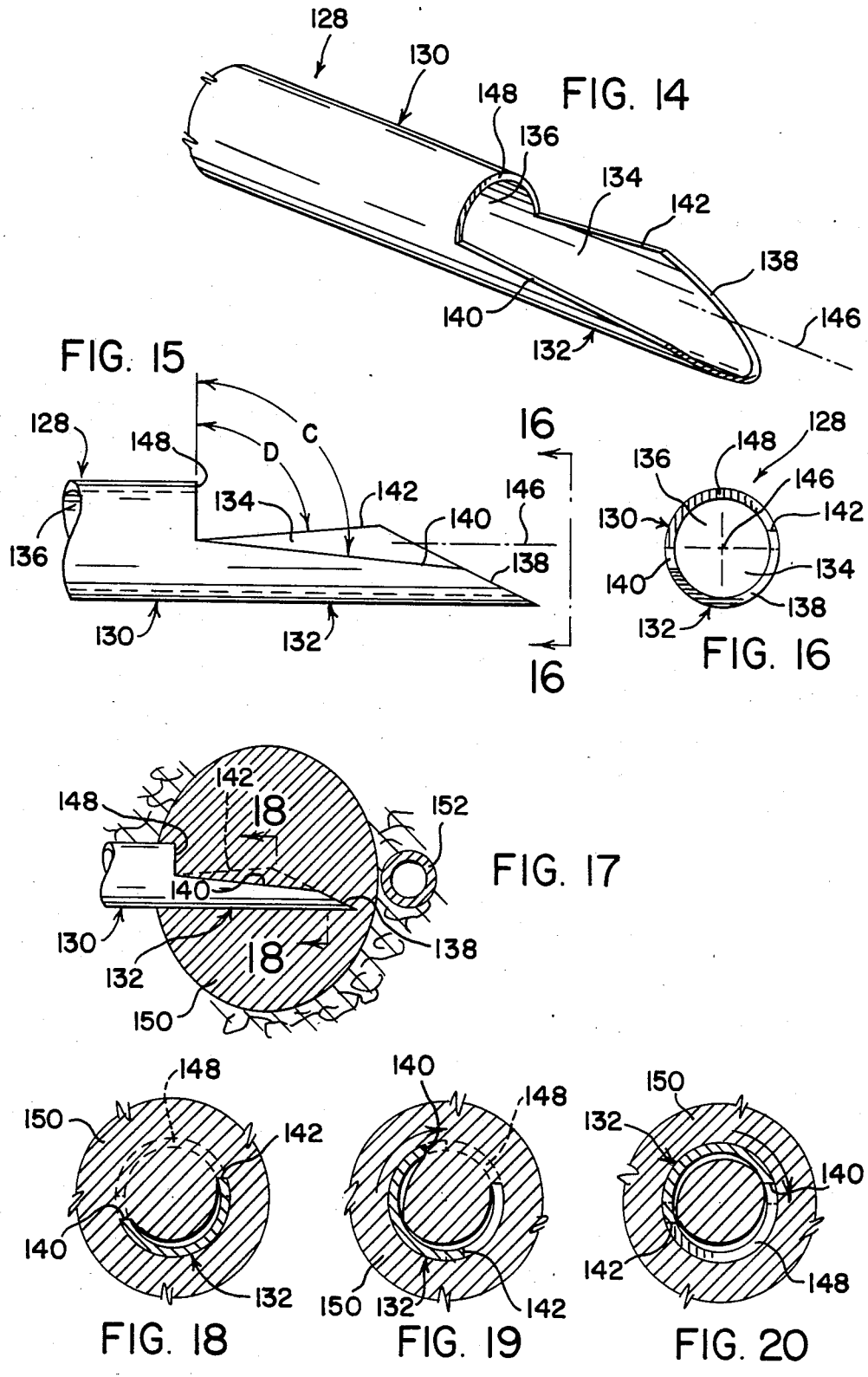

UNIVERSAL BIOPSY NEEDLE

This is a continuation, of Ser. No. 705,051 filed Feb. 25, 1985 which is a continuation-in-part of prior application Ser. No. 625,356, filed June 27, both are now abandoned.

BACKGROUND

The invention relates to tissue sampling devices and, in particular, to a biopsy needle for extraction of tissue samples from the human body without surgery.

The present invention finds particular utility with regard to biopsy devices for removing tissue samples from the human body; however, the invention has much broader applications and may be used for selective extraction of tissue samples from other living matter, such as animals, and for postmortem use with regard thereto.

Biopsy instruments in many forms are well known for extracting discrete tissue samples from a human body for microscopic or growth examination of the tissue for diagnostic purposes. Generally, such biopsy instruments take two forms. In one form, the instrument includes a cylindrical cannula having a circumferentially sharpened distal end defining an axial opening substantially coextensive with the interior passage of the cannula. The cannula is inserted into the tissue where the sample is desired and a vacuum is applied to the cannula passage. While maintaining the vacuum, the cannula is withdrawn thereby extracting the tissue which has entered at the distal end of the passage. This is commonly known as end cutting biopsy sampling. In another form, the cannula is provided with a closed or open pointed end and an opening along the side thereof distant from the end. The cannula is inserted into the region where the sample is desired and by means of applied vacuum or inherent tissue pressure, the tissue specimen is drawn through the side opening into the cannula passage. By means of interior or exterior cutting blades, the tissue in the pocket is severed. Alternatively, the edge of the pocket may include a cutting surface such that upon withdrawal of the cannula the captured tissue is severed and retained in the passage. This is commonly known as side cutting biopsy sampling.

Still other samplers employ pivoting cutting legs which surround the tissue sample and are forced together by the sliding action of an exterior sheath to sever and recover the tissue sample. All of these forms require distinctly separate sampling techniques which are provided by a readily available, but mutually exclusive, single function instrument.

Side cutting biopsy sampling, in particular, can present certain hazards. With the closed end needles, because the side pocket is spaced from the distal end, the point of the cannula projects beyond the site where the sample is to be taken. If, in the desired sampling position, the sharpened end projects beyond the tissue site, a blood vessel surrounding the site may be pierced. Because the blood vessel is isolated from the sampling pocket, no blood flows into the pocket and out the open end of the cannula. Moreover, upon withdrawal, there is no visible indication of internal bleeding and accordingly no remedial action undertaken. With the open ended needle, two types of problems are possible because the gap is remote from the tip. If the tip penetrates a vessel there may not be a blood vessel at the gap and the procedure might be stopped incorrectly. In a contrary fashion no blood vessel may be at the end so no blood returns but a blood vessel may be at the gap so that when a sample is taken injury to the blood vessel may occur. Recently developed percutaneous procedures permit visual radiological observation of the instruments inside the body. Biopsy sampling in particular lends itself to such monitoring. However, because of the distance between the tip and the pocket, it may not be possible to accurately locate the pocket at the desired sampling site without incurring the risk that the gap or distal end may penetrate surrounding blood vessels, which are frequently not visible on the radiological monitors. Further, problems are encountered in retrieving only lesion tissue without also severing normal tissue. Because it is not possible to radiologically monitor the position of the pocket, it is possible to align outside the area of tissue and thereby sever and retrieve normal tissue as well. This complicates and may invalidate the resulting diagnosis. Further, the characteristics of lesion tissue vary and may be determinable only during the biopsy procedure. While some tissue is resilient, other tissue may be hard and resistant to penetration. When unexpectedly encountered, the initial instrument may not be suitable for the biopsy and a substitute, specially adapted instrument must be used.

The present invention overcomes the aforementioned deficiencies of the prior art by providing a biopsy needle which readily penetrates and severs tissues of varying texture characteristics and which can be used to provide both end cutting and side cutting biopsy sampling as required and under conditions which permit the area of the cutting action to be accurately radiologically monitored with reference to the instrument position.

More particularly, cannulas according to the present invention are provided with axially and circumferentially open distal ends. The distal end is defined by a beveled tip, the proximate ends of which are contiguous with circumferentially spaced, longitudinally extending cutting surfaces. The channel wall sections may be ground to provide greater sharpness. These walls are preferably sectioned by grinding of the cannula cylinder to define the tip and the cutting surfaces. The axial length of the tip and the cutting surfaces defines the operative length of the cutting surface. The shape of the walls constitutes a radiological profile which can be accurately visually monitored to determine the position of the channel within the lesion. By selecting a channel length commensurate with a lesion site, it can be readily assured that the cutting action of the cannula will take place entirely within the confines of the lesion tissue without concurrent cutting of the normal tissue therearound. In a single cannula embodiment, a stylet is concentrically located in the passage of the cannula and the combination inserted to the edge of the lesion tissue. The stylet is then withdrawn and the cannula axially inserted into the lesion to the desired depth with the beveled tip axially severing the tissue therealong. Thereafter, the cannula is rotated about its axis and the leading or distal cutting edge and the tip are effective to circumferentially sever the circumscribed tissue. After severing, a vacuum is applied to the proximal end of the cannula and the severed tissue is drawn into the needle and thus retained therein during withdrawal of the instrument. Should a blood vessel be nonetheless inadvertently punctured during use of the needle, blood will flow into the passageway and/or out the proximal end of the cannula. This provides a visual warning to the surgeon such that prompt corrective procedures may be undertaken. The cutting action described above provides for the side cutting mode of operation.

The biopsy needle may also employ two concentric cannulas each having a common distal channel profile. The dual cannula device may employed for both side cutting sampling or end cutting sampling. To provide for side cutting, the cannulas are inserted to the lesion site. Thereafter, the cannulas are relatively rotated and the tissue is circumferentially severed by the cutting action between the passing leading edges of the cannulas. Alternatively, the cannulas may be aligned in opposed relationship with the distal walls forming a continuous outer surface and the distal tips providing for axial cutting action during insertion. Upon application of a vacuum, the severed lesion tissue will be drawn into the cannula passage and extracted upon withdrawal of the instrument. Accordingly, a common distal end configuration for the cannulas is provided which enables both sampling techniques to be performed with a single instrument, as elected or required under the biopsy conditions, and in a manner which permits accurate placement and radiological monitoring of the instrument at the biopsy site.

Accordingly, an object of the present invention is the provision of a biopsy needle adapted for both side cutting and end cutting tissue samples.

Another object of the invention is the provision of a biopsy device in which the cutting site can be accurately visually monitored.

A further object of the present invention is the provision of a distal end for a biopsy needle which has an axially and circumferentially open channel defining cutting surfaces effective upon axial or rotational movement of the needle for severing tissue at a biopsy site.

Yet another object of the present invention is the provision of a biopsy needle wherein concentric cannulas can be selectively oriented for both end cutting and side cutting biopsy sampling.

Still another object is the provision of a method for biopsy sampling wherein the size of the lesion tissue to be sampled is radiologically determined, a distal end of a biopsy cannula is provided with a distal cutting channel smaller in size than the lesion, the distal end being inserted into the lesion and the position of the channel radiologically monitored until it is located wholly within the lesion, the cannula thereafter manipulated to sever the adjacent tissue in the lesion, and thereafter applying a vacuum to the cannula during withdrawal to extract the tissue from the lesion site.

BRIEF DESCRIPTION OF THE DRAWINGS

These and other objects and advantages will become apparent from the description of the preferred embodiments taken in conjunction with the accompanying drawings in which:

FIG. 1 is a perspective view of a single cannula biopsy needle having an operative distal end according to one embodiment of the present invention;

FIG. 2 is an enlarged side elevational view of the operative distal end of the cannula shown in FIG. 1;

FIG. 3 is an elevational view taken along line 3—3 of FIG. 2;

FIGS. 4a, 4b and 4c are side views of the operative distal ends of prior art biopsy needles in use;

FIG. 5 is a side view of the distal end of the embodiment shown in FIG. 1 in use illustrating the puncturing of a blood vessel.

FIG. 6 is a side view of the operative distal end of the embodiment shown in FIG. 1 in use within a lesion;

FIG. 7 is a perspective view of a double cannula biopsy needle having an operative distal end according to another embodiment of the present invention;

FIG. 8 is an end view of the distal ends of the cannulas of FIG. 7 showing the cannulas oriented for performing side biopsy sampling;

FIG. 9 is a view similar to FIG. 8 showing the distal ends of the cannulas oriented for performing end cutting biopsy sampling;

FIG. 10 is a side view of the operative distal end of the double cannula positioned in use in accordance with the orientation of FIG. 9;

FIG. 11 is a side elevational view of the distal end of the single cannula shown in FIG. 1 using a conically pointed stylet.

FIG. 12 is a view similar to FIG. 11 showing the distal end of the single cannula carrying a stylet having a beveled face complementary to the distal tip;

FIG. 13 is a view similar to FIG. 11 showing the cannula carrying a stylet having an end face of differing inclination than the distal tip;

FIG. 14 is a side perspective view of a single cannula biopsy needle having an operative distal end according to a further embodiment of the present invention;

FIG. 15 is a side elevational view of the operative distal end of the cannula shown in FIG. 14;

FIG. 16 is a view taken along line 16—16 in FIG. 15;

FIG. 17 is a side view of the operative distal end of the cannula shown in FIG. 14 in use within a lesion; and, FIGS. 18 through 20 are enlarged cross-sectional views taken on line 18—18 of FIG. 17 showing the side cutting by the cannula during removal of the tissue sample.

DETAILED DESCRIPTION OF THE INVENTION

Referring to the drawings, FIG. 1 shows a biopsy needle 10 including a cannula 12 having an operative distal end 14 according to the present invention. The distal end 14 is formed with an axially and circumferentially opening channel 20 communicating with a central passage 22 in the proximal portion of the cannula 12. The cannula 12 conventionally comprises a thin-walled hollow elongated cylinder of circular cross-section formed of a suitable material such as stainless steel. Such cannulas are available in a plurality of lengths, diameters and wall thicknesses. The proximal end of the cannula, not shown, may be any suitable conventional design adapted for the type of biopsy being performed. For purposes of future reference, the cannula 12 has a longitudinal axis 24 about which the distal end 14 is formed with respect to a vertical plane 26 coincident with the axis 24 and a horizontal plane 28 coincident with the axis 24. The direction along the axial length of the cannula is referred to as longitudinal. The direction of cross-sectional planes through the cannula will be referred to as transverse. In embodiments using cannulas of non-circular cross-sections, a central longitudinal axis would also be present along the length of the cannula.

The distal end 14 of the cannula 12 is formed by the hereinafter described sectioning of the cannula to form the channel 20. The channel 20 is defined by a beveled distal tip 32 and a longitudinal cutting section including circumferentially spaced longitudinally extending cutting edges 34 and 36. The edges 34 and 36 are contiguous with the proximal ends of the beveled tip 32 and extend rearwardly toward the proximal end of the cannula 12. A transverse base edge 38 circumferentially interconnects the cutting edges 34 and 36. In other words, the channel 20 constitutes a selective continuation of the cannula wall defining the central passage 22. The beveled distal tip 32 is perpendicular to a vertical plane through the axis 24 and forms a diherdral angle A with respect to the horizontal plane 28. The cutting edges 34 and 36 are formed by sectioning the cannula cylinder in a plane coincident with axis 24 and the horizontal plane 28. The base edge 38 lies in a vertical plane perpendicular to the axis 24. If desirable, the exposed edges defining the channel may be canted by supplemental operations to provide sharper cutting edges. The distal end 14 thus provides two contiguous cutting portions, namely the cutting section of the edges 34, 36 and the end section of the distal tip 32. These sections also define the overall operative length of the cutting action of the distal end 14. Moreover, it is important that the edges defining the sections are contiguous to provide a continuous transition between the discrete wall sections such that no snags or other impediments to insertion of the needle are created. While the open channel could be defined by a single beveled surface of shallow angle such as shown in FIG. 5, for greater rigidity and ease of insertion, it is preferred to form distinct dihedral surfaces for axial and rotational severing. In this respect, the beveled tip 32 is well adapted for axial insertion with the semi-cylindrical axial profile and beveled angle presenting reduced resistance to axial insertion. It is preferred that the beveled surface bear a significant angle of inclination with respect to the axis 24 in the range of 20°-75° and preferably between 20° and 45°. Although illustrated as being coplanar and coincident with the axis 24, the cutting surfaces may lie in a common plane parallel to or inclined with respect to the axis 24. Further, as illustrated in the embodiment below, each of the cutting edges may be defined by parallel or mutually inclined surfaces.

In any event however, the longitudinal cutting edges 34 and 36 bear a shallow angle with respect to the axis 24 and do not present significant cutting action on the tissue in the vicinity of the channel 20 during axial insertion of the cannula in the manner hereinafter set forth. Moreover, by extending the shallow angle of inclination, the defined cutting surfaces are extremely effective for circumferentially severing the sample retained therein during rotation of the cannula. Further, by having the beveled tip 32 span a sector of 180° or greater, it is possible to concentrically arrange the double cannulas in opposed relation as hereinafter described thereby providing a continuous cylindrical profile for end sectioning tissue samples.

The cannula thus described above provides substantial improvements over the prior art site sampling cannulas which are representatively illustrated in FIGS. 4a, b and c In FIG. 4a, the prior art biopsy needle 50 includes a conical distal tip 52 terminating with a cylindrical body 54 having an alongated circumferential side pocket 56 which communicates with the interior passage of the needle. In use, the needle 50 is inserted into the body with the conical distal tip 52 piercing into a lesion 58. As illustrated, the lesion 58 may be bounded by a blood vessel 60. In the event that the tip 52 projects beyond the lesion 58, the vessel 60 may be punctured causing hemorrhaging. Inasmuch as the needle passage is isolated from the hemorrhaging site, no blood will flow into the passage and no indication of the blood loss will be apparent during use or after withdrawal. Further, because of the length between the tip 52 and the proximal end of the side pockets 56, the side pocket 56 may not be totally contained within the lesion 58. Accordingly, when the tissue within the pocket 56 is severed by means not shown, normal as well as lesion tissue will be sampled. Further, because the side pocket 56 does not present a distinguishable radiological profit, monitoring of the position thereof is difficult.

In FIG. 4b, if the needle tip 50b of needle 50b penetrates a blood vessel 60b, blood will return and the procedure will be incorrectly stopped even though the pocket 56b is properly positioned in lesion 58b. Alternatively, in FIG. 4c, blood will not return from tip 50c but if the sample is taken the blood vessel 60c in lesion 58c will be cut at the pocket 56c.

The aforementioned hemorrhaging detection is overcome by the open channel as illustrated in FIG. 5. Therein, the cannula 12 with the distal end 14 with the circumferentially and axially opening channel 20 has the tip 32 projecting through the lesion 58 and puncturing the blood vessel 60. Accordingly, blood will flow rearwardly through the cannula passage 12 and out the proximal end of the cannula 12. This will provide visual indication, in use or after withdrawal, that such an incident has occurred and the appropriate remedial action may be promptly undertaken. FIG. 6 illustrates the use of the subject biopsy needle in the manner intended. Therein, the lesion 58 has been radiologically sized. Based on this measurement, a distal end length and cannula diameter is selected which will permit the channel 20 to be totally located within the lesion 58. Accordingly, the blood vessel 60 will not be punctured and only lesion tissue will be withdrawn. In other words, the axial longitudinal length of the beveled tip 32 and the axial longitudinal length of the cutting edges 34 and 36 is selected to provide an operative distal end length for appropriately locating the cannula at the lesion site. The position of the end of the instrument and the location of the channel can be radiologically monitored by proper orientation of the needle profile. Thereafter, when the channel 20 is accurately positioned within the lesion 58, the cannula 12 is rotated about the longitudinal axis 24 to circumferentially sever lesion tissue. Preferably, a partial vacuum is applied to the proximate end of the needle by conventional means. This permits the severed sample to be held within the channel 20 and in the adjacent end of the cannula for separation and withdrawal during removal of the needle. While a vacuum may be applied to draw tissue sample into the channel 20 prior to severing, the open configuration normally makes this unnecessary inasmuch as the resiliency of the lesion will generally cause the lesion tissue to substantially occupy the area circumscribed by the cutting edges. The sizes of the sample withdrawn will depend on the operative length of the distal channel as well as the diameter of the needle. For greatest versatility, the needles should be available in a variety of sizes and needles according to the invention having conventional diameters and channel lengths of 2-20 millimeters should preferably be provided.

Referring to FIG. 7, a biopsy needle 80 is provided with an inner cannula 82 and an outer cannula 84 concentrically disposed about a central longitudinal axis 85. The inner cannula 82 has a sliding and rotational fit with respect to the outer cannula 84. The inner and outer cannulas 82 and 84 are sectioned in accordance with the profiles discussed with reference to FIG. 1. In other words, both have sectioned tips and cutting edges defining axially and circumferentially opening channels 86 in the distal ends thereof. This provides for a geometrically similar configuration, which when similarly oriented, provides for coplanar tips 87, cutting edges 88, 89 and base edge 90. In other words, the cannulas are prepared in geometrically similar configurations but are not identical because of the differences in relative diameters. The double cannula biopsy needle 80 may be inserted into a lesion as described above with reference to the single cannula design. Thus, with the cannulas 82, 84 aligned as shown in FIGS. 7 and 8, both cannulas are simultaneously axially inserted into the lesion 91. When properly positioned as observed by radiological monitoring, the inner cannula 82 and outer cannula 84 are relatively rotated about the axis 85. When the adjacent cutting edges pass each other, the tissue therebetween is circumferentially severed with a scissoring action resulting in the aforementioned side cutting biopsy technique. This side cutting action is particularly useful in sampling soft tissue lesions. After severing, the tissue may be drawn into and retained in the channel by application of a vacuum to the proximal end such that the severed tissue is securely retained and separated by withdrawal of the biopsy needle 80.

Alternatively, the inner cannula 82 and the outer cannula 84 may be positioned with the distal ends in diametrically opposed relationship as shown in FIGS. 9 and 10. In this position, the edges defining the cutting section provides a continuous outer periphery and an axial continuation of the internal passage of the inner cannula 82. The opposed diverging beveled tips 87 will act as effective axial cutting blades as the cannulas are simultaneously inserted into the lesion 91. Upon axial insertion to the desired depth and application of a vacuum to the proximal end, the severed tissue will be drawn into the passage thus defined, to provide for the end cutting biopsy technique for severing lesion samples. While maintaining the vacuum, the cannulas 82, 84 are withdrawn thereby securely holding and separating the severed sample. Thus, it will be apparent that the dual cannula design is well adapted for performing both biopsy techniques with a single instrument design.

It is also desirable to employ a stylet as part of the invention. The stylet performs the function of filling the inside of the cannula to prevent entry of tissue or other materials until the cannula is in position. For example, in the single cannula or double cannula embodiments, the distal end of the cannula carrying the stylet is inserted to the edge of but not penetrating the lesion. The stylet is then withdrawn and the cannula further inserted into the lesion to the desired depth and thereafter rotated to sever the tissue. The stylets may have various distal end configurations to aid in the insertion of the instrument. Three stylet designs usable with the embodiments described herein are shown in FIGS. 11 through 13.

Referring to FIG. 11, a biopsy needle 100 having a cannula 102 has a stylet 104 telescopically carried therein. The stylet has a conical tip 106. The conical design of the tip 106 helps spread the tissue during insertion of the biopsy needle. The beveled end 107 has a conical surface 108 forming a continuation of the conical tip 106 thereby eliminating a sharp point which could tear the tissue.

Referring to FIG. 12, the cannula 110 telescopically carries a stylet 112 having a beveled end 114 of the same angle as the beveled tip 116 of the cannula 110. The similarity in the beveled angle aids the insertion of the cannula while minimizing the disturbance of tissue adjacent to the track established by insertion of the needle to the lesion.

Referring to FIG. 13, a stylet 120 carried by the cannula 122 has a beveled tip 124 formed at an angle steeper than that of the tip 126 of the cannula 120. The variation in the tip angles distributes between the cannula 122 and the stylet 120, the tissue cutting action during insertion of the needle to the lesion. The tip 126 has a reversely beveled surface 128 to reduce any tissue tearing action during insertion.

A further embodiment of the biopsy needle is shown in FIGS. 14 through 16. Therein, the biopsy needle 128 includes a cannula 130 having a distal end 132 forming an axially and circumferentially opening channel 134 communicating with the cannula interior passage 136. The channel 134 of the distal end 132 is defined by a beveled distal tip 138 and longitudinal cutting edges 140 and 142 which are contiguous with and constitute continuations of the distal tip 138. The cutting edges 140 and 142 have varying inclinations with respect to the cannula axis 146 and a vertical base edge 148 perpendicular thereto. More particularly, the edge 140 lies in a plane inclined downwardly from the axis 146 toward the distal end and bears an angle C with respect to the plane of edge 148. The cutting edge 142 is inclined upwardly toward the distal end with respect to the axis 146 and bears an angle D with respect to the edge 148. As in the previous embodiments, the edges 140, 142 and the tip 138 may be further sharpened to increase their cutting effectiveness. While the edges 140 and 142 are illustrated as being symmetrically disposed above and below a horizontal plane containing the axis 146, the edge may be individually and independently inclined and may both have upward or downward inclinations. Because of the relative inclinations of the cutting walls 140 and 142, lesser torque or twisting force is required during rotational severing of the cannula. Moreover, when used in a double cannula design, the passing of the leading cutting edges produces a more affirmative cutting action during the recovery of the sample. In use, as shown in FIG. 17, the cannula 130 is inserted by radiological monitoring into the lesion 150 in the position as shown with the length of the channel being selected to place the same entirely within the confines of the lesion and thereby spaced from any adjoining blood vessels 152. While either of the edges 140 or 142 may be used as the distal or leading cutting edge, the downwardly inclined wall 142 is generally preferable inasmuch as it has a lesser discontinuity with the cutting action of the tip 138. Thus, as shown in FIG. 18, sample tissue from the lesion 150 will be retained within the projected envelope through one revolution as shown in FIGS. 19 and 20. The tissue will be circumferentially severed by the cutting edge 140 as shown in FIG. 20.

The above described embodiments of biopsy needles may be used in numerous ways making them essentially universal. It can readily sample both hard and soft tissue lesions and its operative distal end can be accurately positioned entirely within a lesion by the use of radiologic observation. Moreover, numerous sampling procedures may be employed. For example, the concentric cannula embodiments used with a stylet may be inserted to the edge of a lesion and the stylet withdrawn. With the cannulas similarly aligned, the needle is advanced to position the operative distal end at the desired location within the lesion as observed radiologically. Thereafter, the outer cannula is rotated to sever the tissue in the aforementioned manner. By then withdrawing only the inner cannula, preferably with the partial vacuum applied, the severed tissue sample may be withdrawn and examined. If the tissue sample is unsatisfactory, the inner cannula may be reinserted and another sample taken without establishing a new needle track. This would constitute operation of the double cannula with the side cutting sampling technique. In an alternative procedure, after the dual cannulas and stylet have been inserted, the stylet is withdrawn and the cannulas are relatively rotated to the diametrically opposed end configuration. The needle is thereafter further inserted to axially sever the specimen. Vacuum may be applied to the inner cannula to draw tissue into the needle. However, the same is not generally required during this end cutting technique. Vacuum pressure however, as previously mentioned, is useful in retrieving severed specimens after completion of the biopsy cutting. The aforementioned procedure can also be performed in sequential fashion wherein the outer cannula is first advanced into the lesion and its position radiologically monitored. This will axially sever the lower half of the desired lesion sample. The inner cannula is then rotated to produce the diametrically opposed alignment configuration shown in FIG. 7 and it is thereafter independently advanced into the lesion to the same insertion depth as the outer cannula. This movement of the inner cannula then axially severs the upper portion of the lesion sample. The stylet is then withdrawn and a partial vacuum applied to the inner cannula. Both cannulas are then withdrawn as a unit with the severed tissue sample being held in the cannulas by vacuum. Numerous other procedures may be employed with the embodiment of the inventive biopsy needle by using the above described, open ended needle, instead of the side opening biopsy needles of the prior art, thereby providing a great number of simple, but versatile, procedures through which lesion specimens may be simply and effectively obtained.

It is apparent that using the aforementioned axially and circumferentially opening channel with its discrete cutting edges, the retrieval of tissue samples may be accurately and conveniently undertaken. Beneficial angles for the various cutting edges, the use of concentric cannulas and the desirability of employing the side cutting or the end cutting techniques will vary according to the nature of the tissue sample desired. Accordingly, it is anticipated the range of tip and cutting angles can be selected to optimize the cutting function for the particular operation being performed without departing from the spirit of the invention as described above.

Having thus described the invention, it is claimed:

1. A single cannula biopsy needle adapted for both end cutting and side cutting of a tissue specimen from a tissue mass, said biopsy needle comprising:

a hollow thin wall cylindrical cannula of open ended configuration and having a center passage and a longitudinal axis, a distal end on said cannula forming a circumferentially opening and axially open ended continuous channel, said channel being defined by a frontal tip section and an intermediate cutting section, said frontal tip section having a frontal cutting edge lying in a plane forming a first acute angle with said longitudinal axis, said intermediate cutting section having first and second longitudinal cutting edges proximally contiguous with and forming proximal angled extensions of the said frontal cutting edge of said frontal tip section, said first and second longitudinal cutting edges being inclined with respect to said axis at a second acute angle lesser than said first acute angle, said frontal cutting edge of said frontal tip section being effective to axially incise a short length of tissue upon forward movement of the cannula along said longitudinal axis into a tissue mass and said first and second longitudinal cutting edges being effective to circumferentially sever the said incised tissue length from said tissue mass upon rotation of said cannula about said longitudinal axis.

2. The biopsy needle as recited in claim 1 wherein said first and second longitudinal cutting edges lie in a common plane.

3. The biopsy needle as recited in claim 2 wherein said common plane is coincident with said axis.

4. The biopsy needle as recited in claim 2 wherein said tip section is symmetrically disposed with respect to said common plane and forms a dihedral angle with respect thereto.

5. The biopsy needle as recited in claim 1 wherein said first and second longitudinal cutting edges are inclined coincidentally with respect to said axis.

6. The biopsy needle as recited in claim 5 wherein said first and second longitudinal cutting edges are oppositely inclined with respect to said axis.

7. The biopsy needle as recited in claim 6 wherein said first and second longitudinal cutting edges are symmetrically inclined with respect to said axis.

8. The biopsy needle as recited in claim 7 wherein said first acute angle is in the range of about 20°–50°.

9. The biopsy needle as recited in claim 1 including a stylet telescopically carried in said passage of said cannula and having a distal end located in said channel.

10. The biopsy needle as recited in claim 9 wherein said distal end of said stylet is conical.

11. The biopsy needle as recited in claim 9 wherein said distal end of said stylet is bevelled at the same angle as said first acute angle.

12. The biopsy needle as recited in claim 9 wherein said distal end of said stylet is bevelled at an angle greater than said first acute angle.

13. The biopsy needle as recited in claim 12 wherein said second acute angle is in the range of about 0° to 20°.

14. The biopsy needle as recited in claim 11 wherein said second acute angle is in the range of 0° to 10° and said first and second longitudinal cutting edges are symmetrically oppositely inclined.

15. The biopsy needle as recited in claim 14 wherein said first edges and second longitudinal cutting edges of both cannulas lie in a common plane.

16. The biopsy needle as recited in claim 14 wherein said first and second longitudinal cutting edges of both cannulas are coincidentally inclined with respect to said axis.

17. The biopsy needle as recited in claim 16 wherein said first and second longitudinal cutting edges of both cannulas are symmetrically inclined with respect to said axis.

18. A dual cannula biopsy needle adapted for both end cutting and side cutting of a tissue specimen from a tissue mass, said biopsy needle comprising:

inner and outer hollow thin wall cylindrical cannulas each having a center passage and a longitudinal axis, said cannulas having generally identical open ended configurations but differing slightly in diameter so as to permit said inner cannula to be concentrically disposed within said outer cannula for relative axial and rotational movement therewithin, each of said cannulas having a distal end forming a circumferentially and axially opening channel, which channel is defined by a frontal tip section and an intermediate cutting section, said frontal tip section having a frontal cutting edge lying in a plane having a first acute angle with said longitudinal axis, said cutting section having first and second longitudinal cutting edges proximally contiguous with said frontal cutting edge of said frontal tip section, both of said longitudinal cutting edges of each said cannulas being parallelly inclined with respect to said longitudinal axis with said incline being at a second acute angle which is less than said first acute angle, said distal ends of said dual cannulas being alignable in a first position wherein the corresponding said sections lie in common planes, said frontal tip sections being effective upon forward movement of the cannulas into a tissue mass to axially incise a short length of said tissue, and said longitudinal cutting edges of said cannulas being effective for circumferentially severing the said incised tissue length from said tissue mass upon relative rotation of said cannulas, said cannulas being alternatively initially rotatable to a second position wherein said cutting sections establish an approximate continuation of the cylindrical proximal portions of said cannulas and the opposed said tip sections thereof define intersecting distal cutting sections which are effective upon axial movement of said cannulas into a tissue mass to sever a tissue specimen therefrom.

19. The biopsy needle as recited in claim 18 wherein said common plane is coincident with said axis.

20. The biopsy needle as recited in claim 18 wherein said tip sections are symmetrically disposed with respect to said common plane and form dihedral angles with respect thereto.

21. The biopsy needle as recited in claim 20 wherein said first and second longitudinal cutting edges of both cannulas are oppositely inclined with respect to said axis.

* * * * *